United States Patent [19]

Raab

[11] Patent Number: 5,251,127
[45] Date of Patent: Oct. 5, 1993

[54] COMPUTER-AIDED SURGERY APPARATUS

[75] Inventor: Simon Raab, Longwood, Fla.

[73] Assignee: Faro Medical Technologies Inc., Lake Mary, Fla.

[21] Appl. No.: 562,213

[22] Filed: Jul. 31, 1990

Related U.S. Application Data

[63] Continuation-in-part of Ser. No. 230,588, Aug. 10, 1988, abandoned.

[30] Foreign Application Priority Data

Feb. 1, 1988 [CA] Canada ................... 557814

[51] Int. Cl.⁵ ............................................ G06F 15/00
[52] U.S. Cl. ............................... 364/413.13; 606/130
[58] Field of Search ...................... 364/413.13, 413.01;
128/782, 774, 653 R, 899, 660.09, 661.09;
606/1, 129, 130; 901/14, 15, 16, 46

[56] References Cited

U.S. PATENT DOCUMENTS

| | | | |
|---|---|---|---|
| 4,068,156 | 1/1978 | Johnson et al. | 901/14 |
| 4,473,074 | 9/1984 | Vassiliadis | 128/395 |
| 4,571,834 | 2/1986 | Fraser et al. | 128/782 |
| 4,659,971 | 4/1987 | Suzuki et al. | 901/16 |
| 4,674,057 | 6/1987 | Caughman et al. | 901/46 |
| 4,698,777 | 10/1987 | Toyoda et al. | 901/14 |
| 4,742,815 | 5/1988 | Ninan et al. | 128/4 |
| 4,762,016 | 8/1988 | Stoughton et al. | 901/15 |
| 4,776,749 | 10/1988 | Wazenberg et al. | 901/14 |
| 4,791,934 | 12/1988 | Brunnett | 128/653 R |
| 4,805,615 | 2/1989 | Carol | 606/130 |
| 4,821,206 | 4/1989 | Arora | 901/46 |
| 4,835,710 | 5/1989 | Schnelle et al. | 901/14 |
| 4,943,296 | 7/1990 | Funakubo et al. | 901/15 |
| 4,955,891 | 9/1990 | Carol | 606/130 |
| 5,078,140 | 1/1992 | Kwoh | 901/16 |

FOREIGN PATENT DOCUMENTS 0322363 1/1985 European Pat. Off. .
0155857 12/1988 European Pat. Off. .
0326768 8/1989 European Pat. Off. .
8809151 12/1988 World Int. Prop. O. .

Primary Examiner—Roy N. Envall, Jr.
Assistant Examiner—Laura Brutman
Attorney, Agent, or Firm—Fishman, Dionne & Cantor

[57] ABSTRACT

To aid a medical practitioner in positioning a surgical instrument or implant when performing surgery on or examining portions of a patient, patient data is developed which identifies the position and orientation of the portion to which surgical procedures or examinations are to be applied. The position and orientation of the instrument or implant is sensed and instrument data is developed from this sensing. The patient data is converted to objective signals to be displayed on a video display, and the instrument data is converted to instrument signals for presenting the position and orientation of the instrument or implant on the same display. Thus, by watching the display, the medical practitioner is aided in manipulating the instrument or implant relative to the portion.

16 Claims, 10 Drawing Sheets

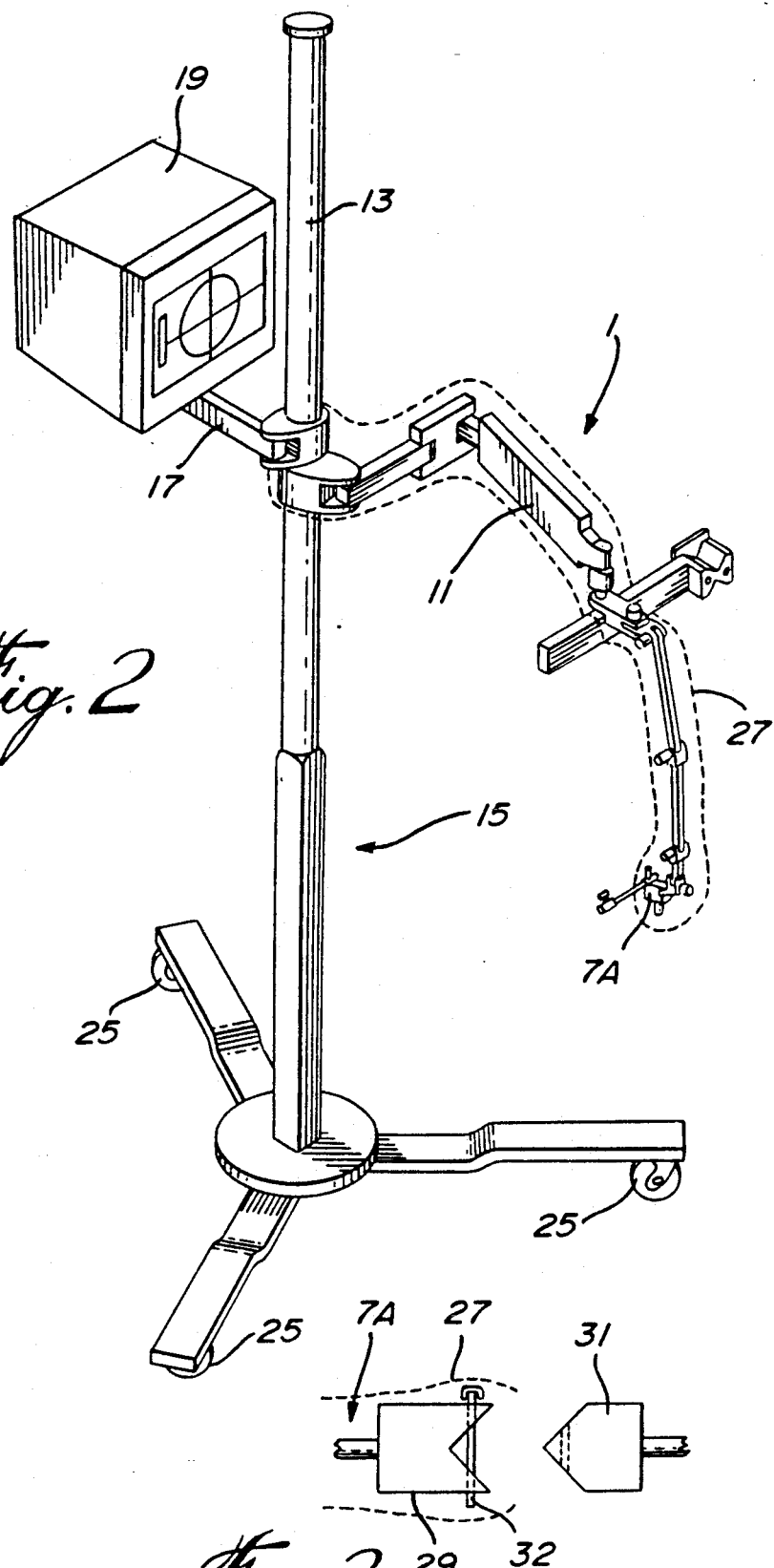

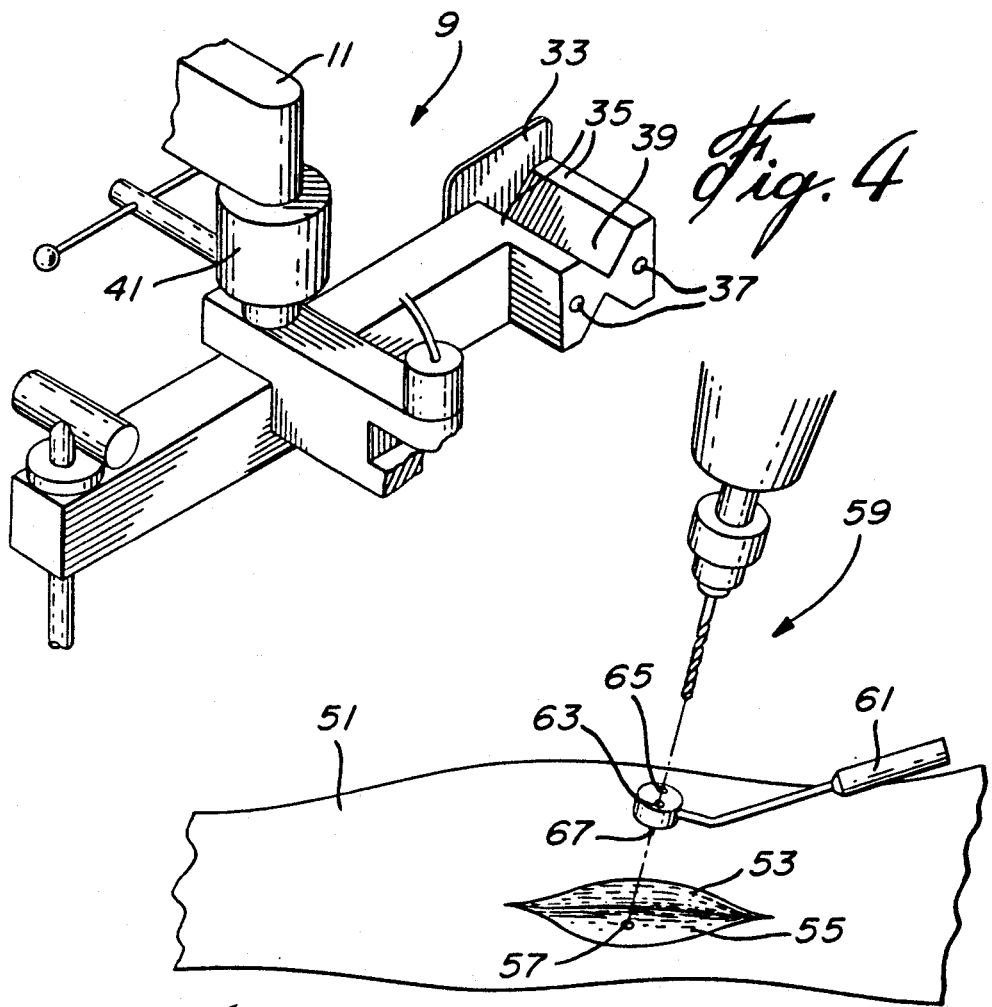
Fig. 4
Fig. 5
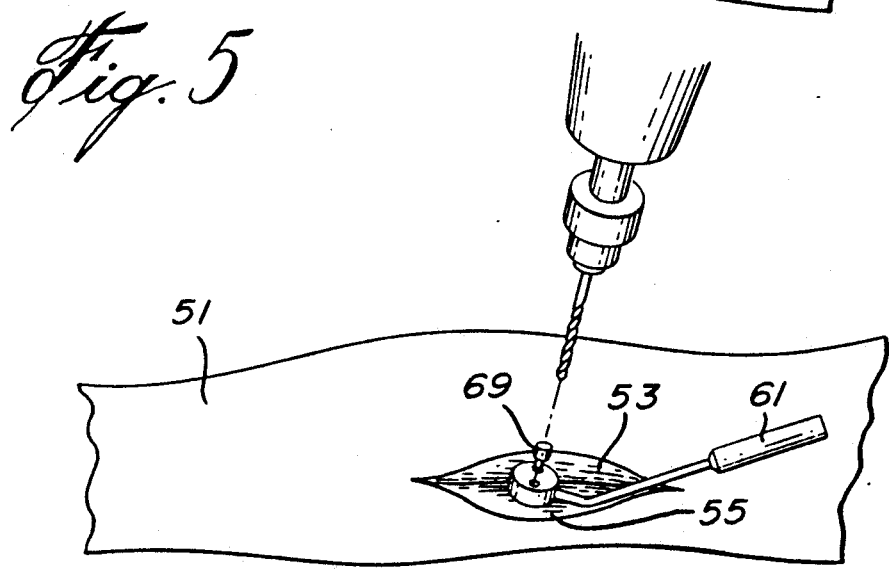
Fig. 6

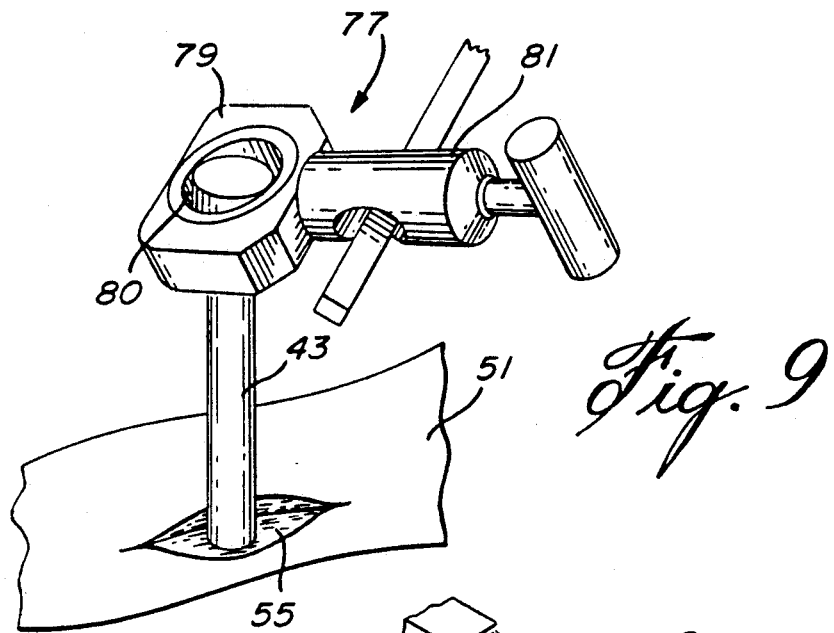
Fig. 9
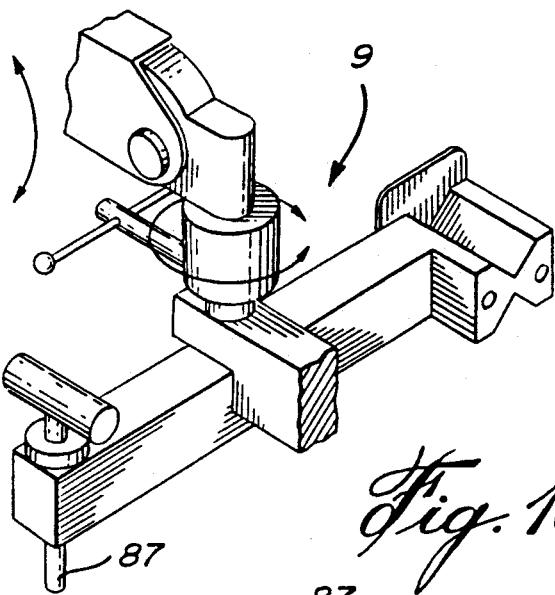
Fig. 10
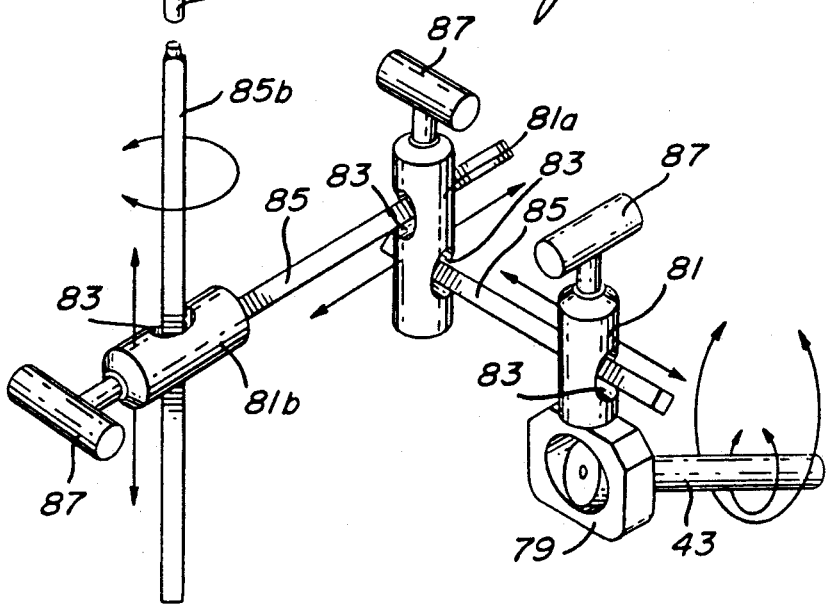

COMPUTER-AIDED SURGERY APPARATUS

The present application is a continuation-in-part of U.S. application Ser. No. 230,588 filed Aug. 10, 1988 now abandoned.

BACKGROUND OF INVENTION

1. Field of the Invention

The invention relates to a computer-aided surgery apparatus. More specifically, the invention relates to such an apparatus which aids a medical practitioner in accurately positioning surgical instruments for performing surgical procedures, or examinations, on a patient.

The invention also relates to a means for connecting a fixed point on a portion of interest of a patient (for example, a fixed point on a leg or arm of a patient) with a fixed point on the apparatus, and for maintaining a known separation between the fixed points, whereby, to maintain a known relationship between the portion of interest of the patient and the apparatus even when the portion of interest of the patient is being moved.

In one embodiment, the means for connecting comprises a linkage mechanism whereby the known separation comprises a fixed separation and the known relationship comprises a fixed relationship.

2. Description of Prior Art

Many surgical fields of orthopedic surgery and neurosurgery, involve the careful placement and manipulation of probes, surgical instruments.

There are available mechanical apparatus which are used for different surgical procedures to help the surgeon guide the surgical instruments to ensure proper alignment. These alignment mechanisms must be referenced to certain anatomical landmarks and the set-up time for the various alignment jigs can represent a significant portion of the total surgical duration.

When surgical procedures are required on, for example, unexposed tumors or the like, fluroscopy is used to indicate to the surgeon the position and orientation of the surgical procedure. This has the disadvantage of exposing a patient and physician to radiation. In addition, the accuracy is less than adequate for precision requirements of the surgery.

In addition, in procedures relating to the cutting of boney parts for the purposes of joint replacement, fracture repair or deformity correction, among others, there is the problem of tool orientation such as drilling from point to point, sawing, locating planes in specific orientations with other planes of specific orientations, etc. The problems of 3-dimensional control of the surgical instruments becomes formidable. As above mentioned, some jigs exist for the performance of limited procedures permitting safe and reproducible orientation of tools. However, those have the disadvantage of being less than adaptable to variations that occur during surgical procedures. In addition, the limits of inaccuracy permissible for satisfactory results during surgery leave many of the currently accepted techniques for surgical instrument control unacceptable.

Although the field of 3-dimensional imaging as represented in the techniques of MRI (magnetic resinence and CAT scans (computer aided tomography) proimaging) vide an abundance of 3-dimensional information concerning the locations of, for example, unexposed tumors, there is presently no interface between this information and the surgical processes which provide remedies. Required is an apparatus which can transpose the information of the 3-dimensional imaging systems from the reference system of the 3-dimensional imaging systems to a reference system of the apparatus.

U.S. Pat. No. 4,473,074, Vasiliadis, Sep. 25, 1984, teaches a device providing a laser beam in the performance of microsurgical procedures. The apparatus of the '074 patent does not have the facilities for providing electronic feedback of 3-dimensional information from 3-dimensional imaging systems for the purposes of presentation and feedback to the surgeon to thereby complete a feedback loop necessary to make full use of the instrument in sophisticated procedures. In addition, the device of the '074 patent can be used only to direct a laser beam at an exposed target, so that it is not applicable for surgical procedures on unexposed portions of a patient.

SUMMARY OF INVENTION

It is therefore an object of the invention to provide a computer-aided surgery apparatus which provides significant improvements over present technologies for aiding a medical practitioner in accurately positioning surgical instruments for performing surgical procedures, or examinations, on a patient such as hole drilling, bone sawing, distance measurement and site location (e.g. point to point distance, blind hole location), and stereotaxic aiming and locating.

It is a more specific object of the invention to provide such an apparatus which includes a computer driven precision instrumented linkage attached to a surgical instrument and providing the surgeon with instantaneous and continuous feedback on 3-dimensional orientation of the tool.

It is a still further object of the invention to provide such a linkage which can also be used as an independent anatomical point digitizer so that important reference landmarks can be located and subsequently used as points of reference for surgery.

It is a still further object of the invention to provide an apparatus which eliminates time-consuming set-up of jigs and other apparatus for guiding the surgical instruments and which apparatus is really an intelligent jig capable of adapting to the vageries and unexpected developments often confronted during surgery.

In accordance with the invention, there is provided a computer-aided surgical device for aiding a medical practitioner in positioning a surgical instrument (power or manual) when performing surgery, or an examination, on unexposed and exposed portions of a patient.

BRIEF DESCRIPTION OF DRAWINGS

The invention will be better understood by an examination of the following description, together with the accompanying drawings, in which:

FIG. 2 illustrates the rolling upright stand, the monitor and the electrogoniometer;

FIG. 3 illustrates one means for connecting surgical instruments to the electrogniometer;

FIG. 4 is a more detailed view of the reference block;

FIGS. 5, 6, 7 and 8 illustrate how the Double Self Indexing Screw (DSIS) is attached to a bone of a patient;

FIG. 9 illustrates the first link to the DSIS;

FIG. 10 illustrates the complete link between the DSIS and the reference block of the apparatus;

DESCRIPTION OF PREFERRED EMBODIMENTS

Figure 1:
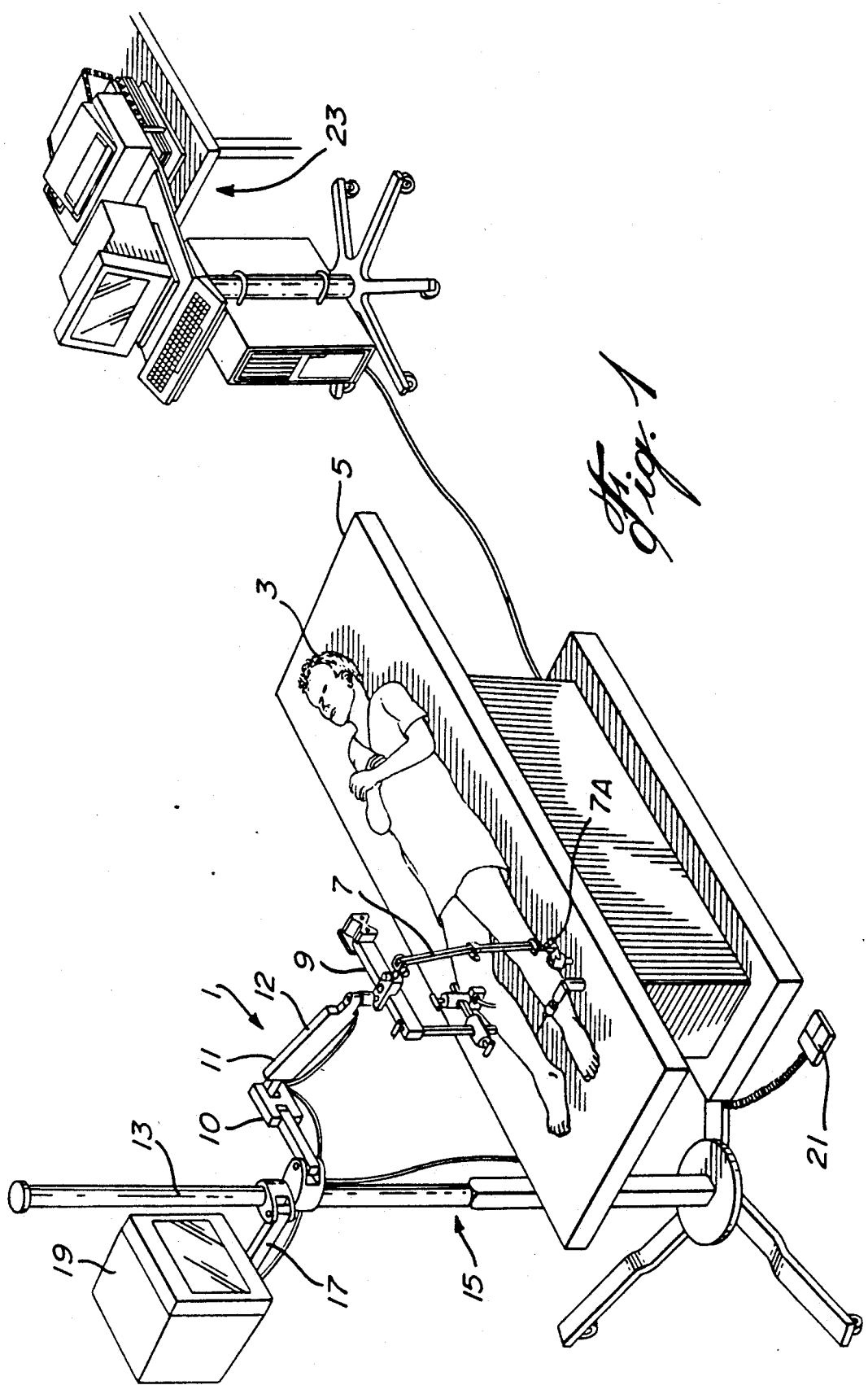
FIG. 1 is a 3-dimensional view of the apparatus in relationship to a patient on an operating table.

Referring to FIG. 1, the apparatus in accordance with the invention, illustrated generally at 1, is disposed for operation on a patient 3 lying on an operating table 5. The apparatus includes an instrument position determining means, for example an electrogoniometer 7 which is preferably of the type described in my U.S. Pat. No. 4,571,834. The six degree of freedom electrogoniometer is designed to provide easy access to any part of the patient in the surgical venue. Surgical instruments are connected to the free end 7a of the electrogoniometer. The other end of the electrogoniometer is connected to a reference block 9 which will be more fully discussed below.

In order to permit movement of the electrogoniometer and reference block to different positions along the patient, the reference block and electrogoniometer are connected to a swinging balanced arm 11. The other end of the balanced arm is connected to an upright post 13 of a rolling upright stand 15. The upright post 13 also supports a monitor support arm 17 which carries a monitor, preferably a colour monitor, 19.

The swinging balanced arm 11 may consist of two portions, 10 and 12, which are pivotal relative to each other, and the portion 10 is pivotal relative to the upright post 13. In a like manner, monitor support arm 17 is pivotal relative to the upright post 13 so that its position can be altered for better viewing by the surgeon.

Foot pedal switch 21 is provided for controlling the displays on the monitor 19, and remote computer 23 performs computations for providing the displays on the monitor.

Turning to FIG. 2, the rolling upright stand 15 comprises rollers 25 to roll the apparatus into different positions alongside the operating table. The electrogoniometer and the swinging balanced arm are covered by a tubular sterile barrier 27 to maintain the integrity of the sterile field around the patient. Instruments which are attached to end 7a of the electrogoniometer are sterilizable in an autoclave to further maintain the integrity of the sterile field.

One mechanism for attaching the surgical instrument to the end 7a of the electrogoniometer is illustrated in FIG. 3. As can be seen, this constitutes a V block 29 disposed within the tubular sterile barrier 27. The instrument itself includes a mating V block 31, and the protruding V of 31 is inserted into the indented V of 29. A pin, such as 32, extends through aligned openings in both 29 and 31. This type of connecting mechanism ensures that the position and orientation of the instrument relative to the electrogoniometer is fixed during the entire surgical procedure.

Turning now to FIG. 4, the reference block includes a reference backplate 33, reference top surfaces 35, reference holes 37 and a V-groove drill reference 39. The purpose of these elements of the reference block, as will be seen below, is to determine the position, orientation and length of various ones of the surgical instruments, as well as the security of the installation of the instruments.

It is also seen in FIG. 4 that the reference block is connected to swinging balanced arm 11 by a ball support 41 which includes an internal ball joint so that spherical motion of the reference block relative to the arm 11 is possible.

From a review of the above-referenced U.S. Pat. No. 4,571,834, it will be clear that the position 7a of the electrogoniometer relative to the reference block in a three-dimensional coordinate reference system (or perhaps more accurately a point on the reference block) will constantly be calculated by the computer which receives inputs from the transducers connecting the various portions of the electrogoniometer. It will also be apparent that the dimensions of the surgical instrument, especially the location of the operating portion of the surgical instrument relative to the end 7a of the electrogoniometer, will both be known and verified by tests on the reference block as will be described below. Accordingly, the position of the operating portion of the surgical instrument will be constantly calculated by computer 23, as described in U.S. Pat. No. 4,571,834, and this position can therefore be continuously displayed on the monitor 19.

Figure 7:
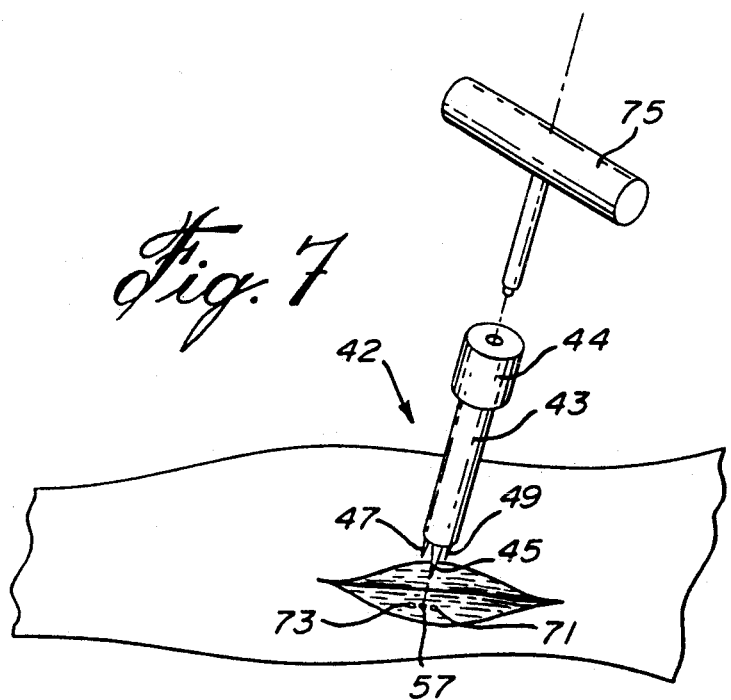
Figure 8:
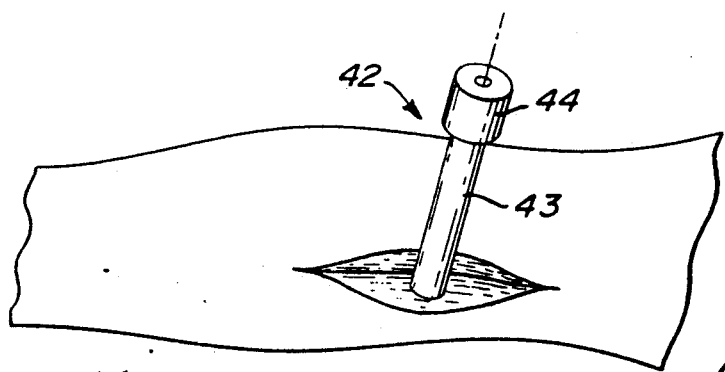

As the position and orientation of the surgical instrument is determined relative to the reference block, it is desirable to maintain a known separation and relationship between the portion of the patient on which operating procedures are to be performed and the reference block. As the portion on which surgical procedures are being performed may have to be moved from time to time during these surgical procedures, it is desirable that the means for maintaining the relationship constitute electrogoniometer means (as discussed below) or a mechanical linkage whereby, when the portion of the patient is moved, the reference block, and therefore the electrogoniometer 7, will move with it. For this purpose, there is provided in accordance with an aspect of the invention, a Double Self Indexing Screw and mechanical linkage illustrated in FIGS. 5 to 12. The Double Self Indexing Screw (DSIS) is illustrated in FIGS. 7 and 8 at 42 and includes a cylindrical portion 43 and a top cap portion 44 as well as a bottom central screw 45 and bottom alignment pins 47 and 49. Screw 45 and pins 47 and 49 are in alignment with each other. The procedure for mounting the DSIS on a portion of interest of the patient is illustrated in FIGS. 5 to 8. Turning first to FIG. 5, the DSIS is to be mounted on, for example, a leg 51. The recent advent of surgical techniques employing arthroscopy in order to minimize soft tissue trauma during surgery requires that the DSIS attachment be made through an incision no greater than 20 mm. Such an incision is shown on the leg 51 with a skin flap 53 lifted to expose bone 55. A first hole 57 is drilled, by drill 59, into the bone 55. A drill guide 61, which includes holes 63 and 65 and guide pin 67, 63, 65 and 67 being in alignment, is then manipulated so that pin 67 is inserted into the hole 57. A second hole is then drilled in bone 55 through, for example, hole 65 of drill guide 61. A reference pin 69 (see FIG. 6) is then inserted into the second drilled hole through hole 65 of drill guide 61 as shown in FIG. 6. A third hole is then drilled in the bone through hole 63. As holes 63, 65 and guide pin 67 are in alignment, the drilled holes will be in alignment as shown at 73, 57 and 71 in FIG. 7.

The DSIS is then connected to the bone by inserting screw 45 into hole 57, pin 47 into hole 73 and pin 49 into hole 71. The screw 45 is screwed into hole 57 by rotation of screw handle 75 which rotates only the screw 45. With the DSIS mounted as shown in FIG. 8, the attachment is both firm and the DSIS is, because of the pins 47 and 49 being inserted in holes 73 and 71 respectively, restrained from rotary motion about its own longitudinal axis.

At times, it may be inconvenient or undersirable to drill holes 71 and 73 for the purpose of mounting the DSIS. Accordingly, an alternative means is provided to replace the DSIS. Specifically, a saw-tooth self-indexing screw is provided.

Figure 8A:
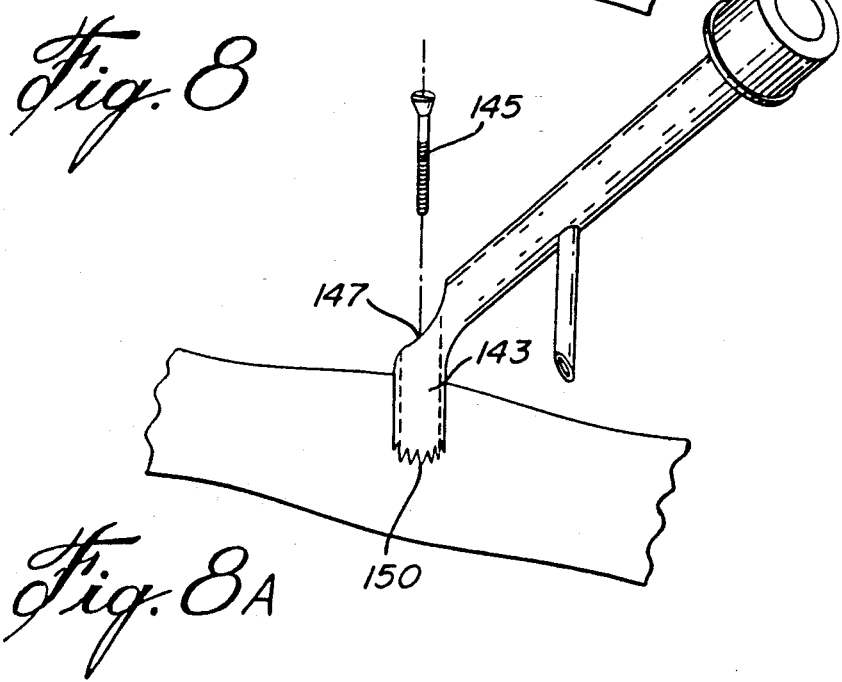
FIG. 8A illustrates an alternative to the DSIS.

Referring to FIG. 8A, it can be seen that the alignment pins 47 and 49 have been eliminated and that the bottom end of the cylindrical portion 43 includes a saw-tooth arrangement 150. Cylindrical portion 143 is shown bent in FIG. 8A, although it could be straight as cylindrical portion 43 is shown in FIG. 8. The bent portion of 143 includes an opening 147 through which screw 145 is passed. Accordingly, when screw 45 is screwed into a hole such as 57 in FIG. 7, the saw-tooth will be embedded in the surrounding bone so that the self-indexing screw will once again be restrained from rotary motion about its longitudinal axis.

The first link from the DSIS to the reference block is illustrated in FIG. 9 and comprises a linear spherical DSIS clamp illustrated generally at 77. The DSIS clamp 77 includes a ball joint arrangement 79 and a clamping member 81.

As seen in FIG. 10, the complete link includes a plurality of clamping members 81 interconnected by shafts 85. Each clamping member includes at least one through hole 83 to receive a shaft 85. The clamping members may also include two transverse through holes 83 as shown at 81a. In addition, the clamping members may also be adapted to receive a shaft at the bottom end thereof as shown in 81b. Each clamping member 81 includes a handle 87, and shaft 85b is insertable into an opening of T member 87 mounted on reference block 9.

Figure 11:
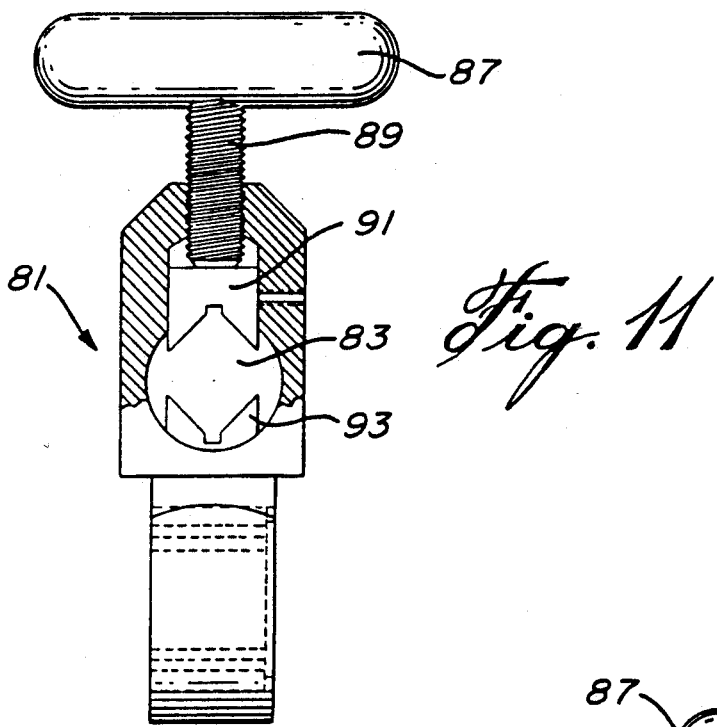
FIG. 11 is a cross-section through XI—XI of FIG. 9 (with the shaft removed)

Referring now to FIG. 11, clamping member 81 includes a screw 89 which is rotatable by handle 87 to move the screw upwardly or downwardly in the interior of the clamping member. Movement of the screw will cause similar movement of V block 91 which is disposed in opposition to V block 93 in the interior of the clamping member 81. With the V blocks 91 and 93 as illustrated in FIG. 11, the cross-sectional shapes of the shafts 85 would be diamond shaped so that, when screw 89 is tightened, the shaft will be firmly grasped between V blocks 91 and 93. Obviously, shafts with different cross-sectional shapes could be used whereupon the shapes of blocks 91 and 93 would be appropriately altered.

Figure 12:
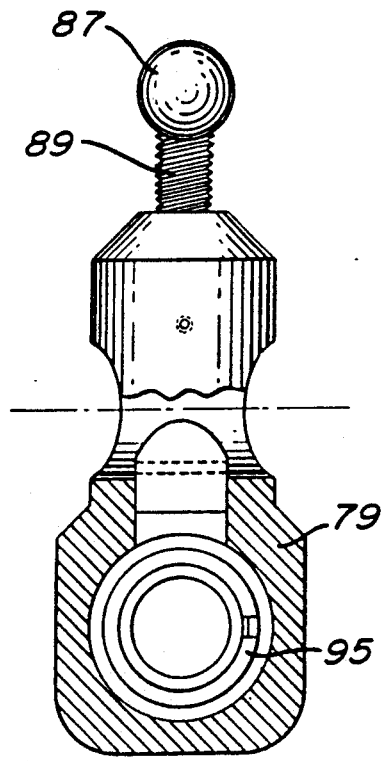
FIG. 12 is a cross-section through XII—XII of FIG. 9 (with the shaft removed)

Referring to FIG. 12, the ball joint arrangement 79 includes a spherical ball bearing joint having a split outer race 95. The head 44 of the DSIS 43 (see FIGS. 7 and 8) is inserted into opening 80 (see FIG. 9) of ball joint arrangement 79. The spherical ball joint permits spherical rotation of the DSOS 43 relative to the ball joint arrangement 79. When handle 87 is rotated to move screw 89 downwardly, downward pressure will also be applied against block 93 to thereby close the split 0-ring 95. Accordingly, the head 44 of the DSIS 43 will be firmly grasped in ball joint arrangement 79.

With the linkage arrangement as illustrated in FIG. 10, there is therefore a fixed and firm relationship between a point on the patient's, for example, leg and the reference block 9. Any motion which is imparted to the leg will therefore also be imparted to the reference block. Thus, for example, if the surgeon should lift the leg while drilling a hole or sawing a plane on the knee, the orientation of the reference plane with respect to the bone will not be disturbed since the reference plane is freely following that bone during this minimum motion. Thus, the surgeon will be able to carry on surgical procedures in his normal customary fashion without disturbing the accuracy or verity of the apparatus.

The apparatus is menu driven and the operation of the apparatus will be described in terms of various menus which are given as examples of how the apparatus may be used.

The Main Menu, illustrated in Table 1 below, into four main categories: Drilling Menu; Sawing Menu; Measurement Menu; Stereotaxic Misc. Menu.

TABLE 1

| MAIN MENU |
| --- |
| *1 - Drilling Menu |
| 2 - Sawing Menu |
| 3 - Measurement Menu |
| 4 - Stereotaxic Misc. Menu |
| 5 - Return to Master Menu |

The menu selections are made by depressing the right pedal of the foot switch 21, depressing the left pedal to confirm. Each time the right pedal is pressed, the pointer will move down one space. When the pointer is adjacent the required menu, then the left pedal is pressed. Selection of an item, for example, the Drill Menu, will result in the presentation of the Drill Menu.

Considering now the Drill Menu, illustrated in Table 2 below, the performance of drilling operations involves four basic steps, namely, digitizing the entry/exit points, installing the drill, installing the drill bit, and drilling the hole. In steps 2 and 3, the configuration, alignment and size of the drill and drill bit are defined.

TABLE 2

| DRILL MENU |
| --- |
| *1 - Digitize Entry/Exit Points |
| 2 - Install Drill |
| 3 - Install Drill Bit |
| 4 - Drill Hole |
| 5 - Return to Main Menu |

To perform the digitization step (step 1) a digitization tip is installed at end 7a of the electrogoniometer. The digitization tip is then calibrated by inserting it into holes 37 of the reference block to verify the axis (orientation) of the digitization tip. It is noted that it is inserted into two holes so that the reproducibility is also confirmed.

The desired entry point is then digitized by placing the end of the digitizer tip at the desired entry position. The desired exit point is similarly digitized.

The end 7a of the electrogoniometer can, of course, accept a variety of different surgical instruments including different drilling instruments. A selected drilling tool is mounted at 7a. A reference pin is then mounted in the drill bit and inserted into holes 37 of the reference block 9. Once again, this verifies the axis (orientation) as well as the security of the installation of the drill mounting on the electrogoniometer. When the axis of the drill has been determined, the reference pin is replaced with the desired drill bit, and the drill bit is then placed in the groove 39 of reference block 9 with the free end of the drill bit up against backstop 33 of the reference block whereby to determine the orientation and length of the drill bit.

Figure 13:
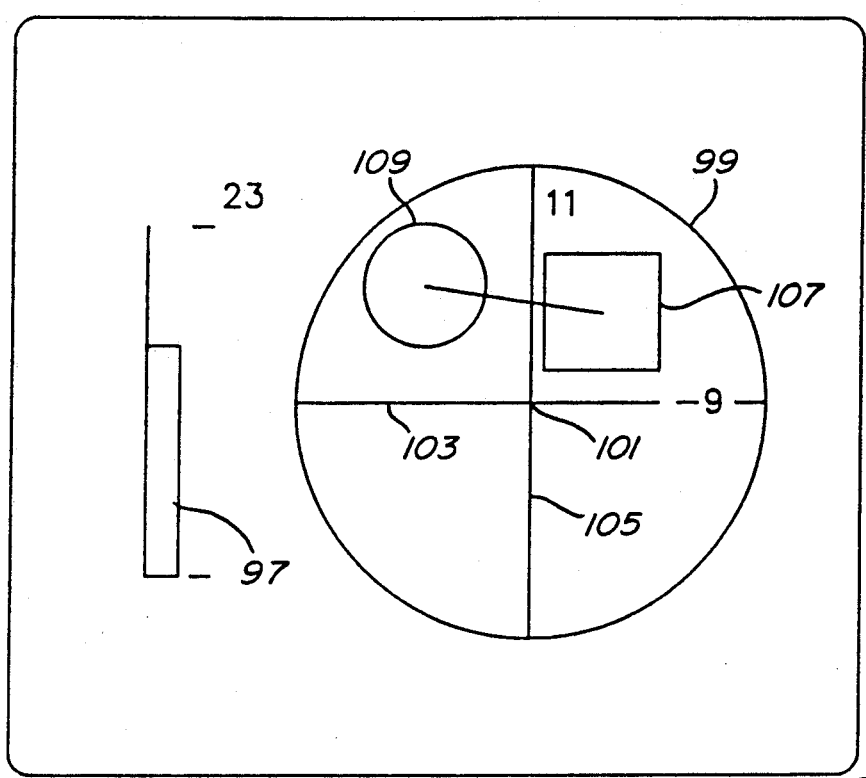
FIGS. 13 and 14 are examples of screen displays to aid in drilling procedures.

When item 4 of Table 2 is selected, the drilling objective or target is displayed on monitor 19 with a penetration depth bar as illustrated in FIG. 13. In FIG. 13, the penetration depth bar is illustrated at 97. The target area is represented by the large circle 99 and the center of the target area 101 is represented by the junction of transverse diameters, or cross-hairs, 103 and 105.

The drill is identified by graphic objects 107 and 109. The square 107 represents the tip of the drill and the circle 109 represents a point behind the tip of the drill, for example, 120 mm behind the tip of the drill, along the axis of the drill. The depth bar is scaled to present the depth of penetration of the drill bit where full scale represents the distance between the entry and exit points as digitized with the procedure above.

Before drilling begins, the drill bit should be moved on the surface of the patient until the square 107 is centered over center 101. The orientation of the drill is then manipulated until the circle 109 is centered in the square 107. When square 107 is centered around center 101, and circle 109 is centered in square 107, then the drill is in the correct position and orientation to proceed from the digitized entry to the exit. This is illustrated in FIG. 14.

It is common that the surface where the entry hole must be made is at an acute angle to the desired axis of penetration. This would make it difficult to start a hole at the entry point in the correct orientation. To accommodate this, a re-referencing protocol is permitted in the drilling operation. The hole is started, at the entry point, but in an incorrect orientation, to provide a starting hole approximately 3 to 5 mm deep in a direction perpendicular to the surface at the entry point. This obviates the problem of drill slippage.

Figure 14:
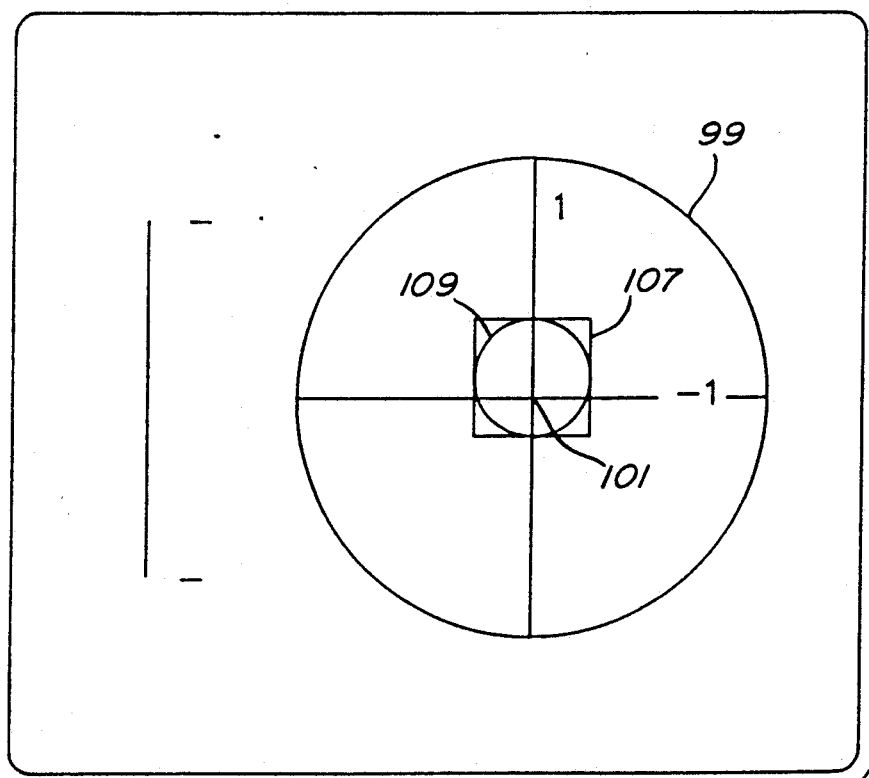

Once the starter hole has been made, the drill is simply redirected in the desired direction of the hole until the display is as illustrated in FIG. 14. Drilling is then continued until the exit point is reached. This procedure provides a simple and effective way of correcting the misalignment of a drilling process due to preliminary drill slippage.

When item 2 of the Main Menu in Table 1 is selected, the Sawing Menu will be displayed on the monitor 19. The Sawing Menu is shown below in Table 3.

TABLE 3

| SAWING MENU |
| --- |
| *1 - Digitize Plane Periphery |
| 2 - Digitize Perp. to Plane |
| 3 - Install Saw and Saw Blade |
| 4 - Saw Plane |
| 5 - Return to Main Menu |

As can be seen, two forms of sawing protocol are defined in this Menu. In item 1 of the menu, a plane is defined by the selection of three points on the perimeter of the plane. In item 2, a plane is defined as being perpendicular to a predetermined axis. The sawing applications range from tibial osteotomies to pre-arthroplasty surface preparation. The multiplanar problems of osteotomies are simply and effectively handled through the concurrent tool control and numerical feedback of the apparatus of the present application.

When item 1 of the Sawing Menu is selected, prompts will be provided on the screen of the monitor 19 for the digitization of points around the perimeter of a desired cut. As in the drilling procedures, digitization of these points are preceded by the measurement of the digitizer tip in the reference holes. The system then prompts for the three points. These three points are then used to define the plane along which the saw cut is to occur.

If item 2 of the Sawing Menu is selected, prompts will be provided to the user to digitize two points defining an axis which is perpendicular to the desired plane. For example, digitizing two points along the tibial crest will result in a saw cut perpendicular to the axis of the tibia. When item 3 of the Sawing Menu is selected, prompts will appear on the screen of the monitor 19 to prompt the user to install a saw and saw blade, and to reference them on the surfaces 35 of reference block 9. As with the installation of the digitizer tip, the saw blade is referenced in two positions, namely, on each of the surfaces one at a time, in order to determine reproducibility and a secure installation.

Figure 15:
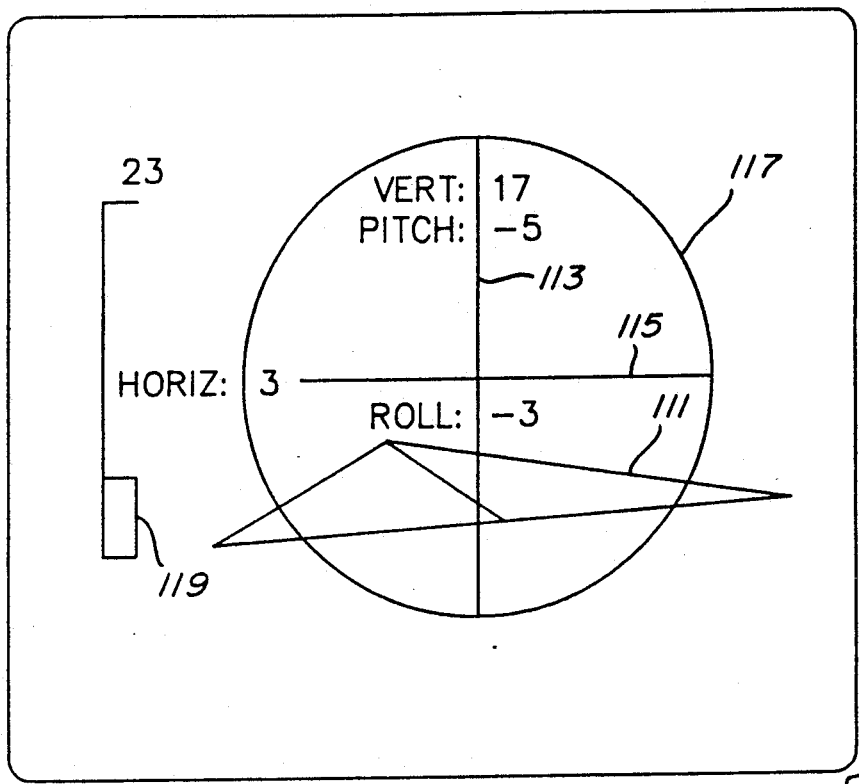
FIGS. 15 and 16 are examples of screen displays to aid in sawing procedures.
Figure 16:
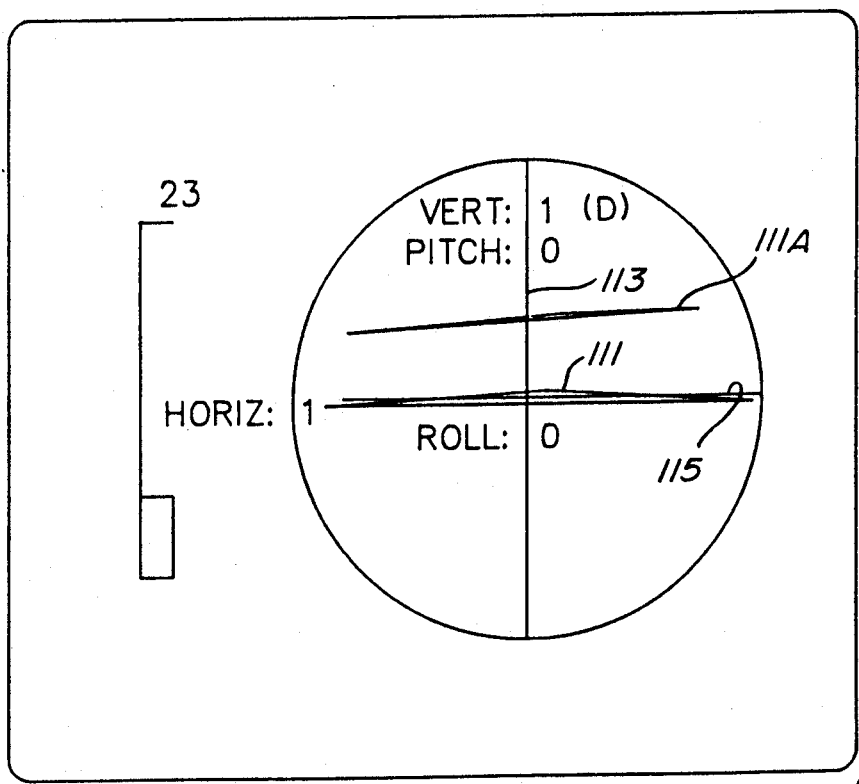

Selection of item 4 of the Sawing Menu will result in the saw display as illustrated in FIGS. 15 and 16. The saw display represents an objective or target similar to that of the drilling display except that the saw blade is not represented by a square and circle of the drill display but rather as a triangular plane 111 representing the flat upper surface of the saw blade. The cross hairs 113 and 115 within the circle 117 represent the desired position of the saw cut while the orientation of the saw symbol 111 must be aligned with the horizontal cross hair 115 in such a manner that only a single line is visible (as shown in FIG. 16) rather than the surface of the saw blade. This assures that the saw blade is parallel to and aligned with the desired sawing plane in the correct position for sawing.

A sawing depth bar 119 represents the depth of penetration of the saw blade from its original entry point. In one embodiment, full scale of the depth bar is 100 mm. The sawing depth bar is not scaled to a desired depth since very often this cannot be measured or is unknown.

The orientation of the saw blade with respect to the desired sawing plane is defined graphically by the triangle 111 and numerically by three numbers displayed about the target. The vertical displacement of the saw blade above or below the desired line (i.e. away from or towards the surgeon) is displayed at the top of the circle 117 while pitch is displayed below the vertical display and roll is displayed below the horizontal line 115. The symbols permit the accurate definition of a cutting plane with respect to a premeasured cutting plane. As is often the case in an osteotomy, a precise cut of a specific angle with respect to a previous cut is the difference between a success or failure. The ability to sustain a known cutting plane in three axes is imperative to the successful operation of a typical osteotomy.

To provide a second cut parallel to a first cut, the vertical position of the saw may be referenced by moving the saw blade up or down (away from or towards the surgeon) from the predetermined saw plane to a previously determined distance D as indicated on the sawing target. Under these circumstances, a second line 111a, parallel to the horizontal line 115, will be displayed. Also, the numeral besides the vertical display will be changed to D. When the saw is now operated, a cut parallel to the first cut and at a distance D away from the first cut will be effected.

The Measurement Menu is selected by selecting item 3 of the Main Menu of Table 1. The Measurement Menu is shown in Table 4.

TABLE 4
MEASUREMENT MENU

*1 - Point to Point Distance
2 - Spinal Curvature
3 - Return to Master Menu

The Measurement Menu may contain a number of generic and specific measurement applications of general use in various forms of surgery. Table 4 illustrates two such applications: Point to Point Distance and Spinal Curvature. When item 1 of the Measurement Menu is selected, the point to point distance screen will be displayed on the screen of the monitor 19. The first step in this procedure is to calibrate the digitizer tip by inserting the digitizer tip into the reference holes 37 of the reference block 9 as above-described with respect to the drilling procedure.

When the first point is digitized, a live digital representation of the vector distance from the original reference point (of the reference block 19) to the current point (the first point) will be presented on the screen of the monitor 19. The tip can be rereferenced simply by pressing the left half of the foot switch 21 at which time the current position of the digitizer tip becomes the reference point. The screen will then prompt the digitization of point 2.

Figure 17:
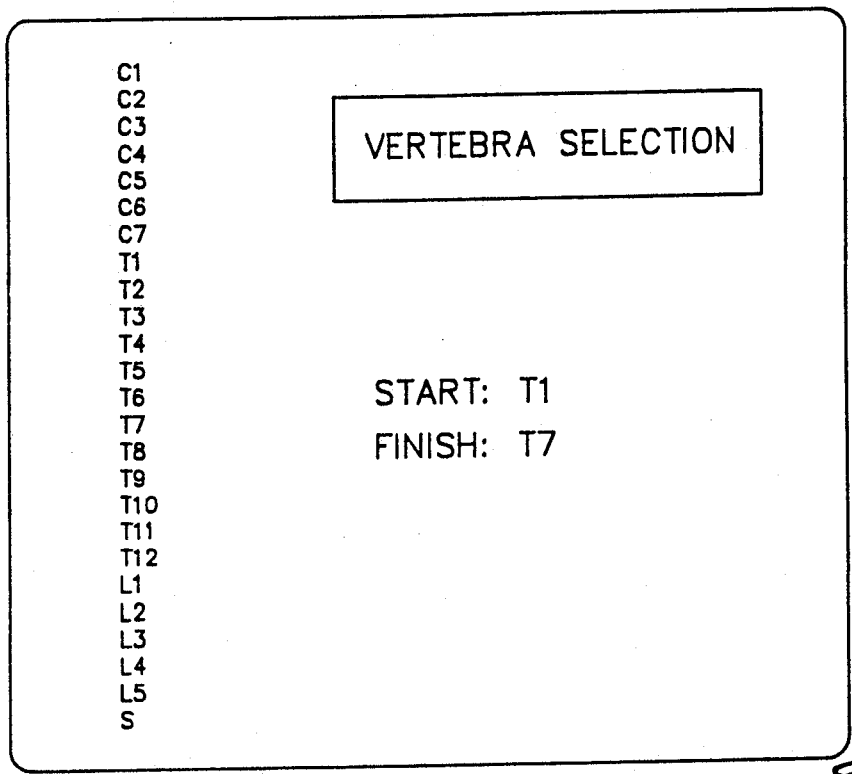
FIGS. 17 and 18 are examples of screen displays to aid in spinal curvature measurement procedures.

Selection of item 2 of the Measurement Menu will result in the prompting for the performance of a spinal curvature measurement. The measurement procedure is employed during surgical procedures relating to the correction of scoliosis curves in an effort to give a direct feedback to the surgeon as to the degree of curvature and correction which is obtained. As usual, the system will first request that the digitizer tip be mounted and calibrated. The mounting and calibration steps are followed by a scan along the spine of predetermined length as determined by the selection of the starting and finishing vertebrae using the screen illustrated in FIG. 17.

Figure 18:
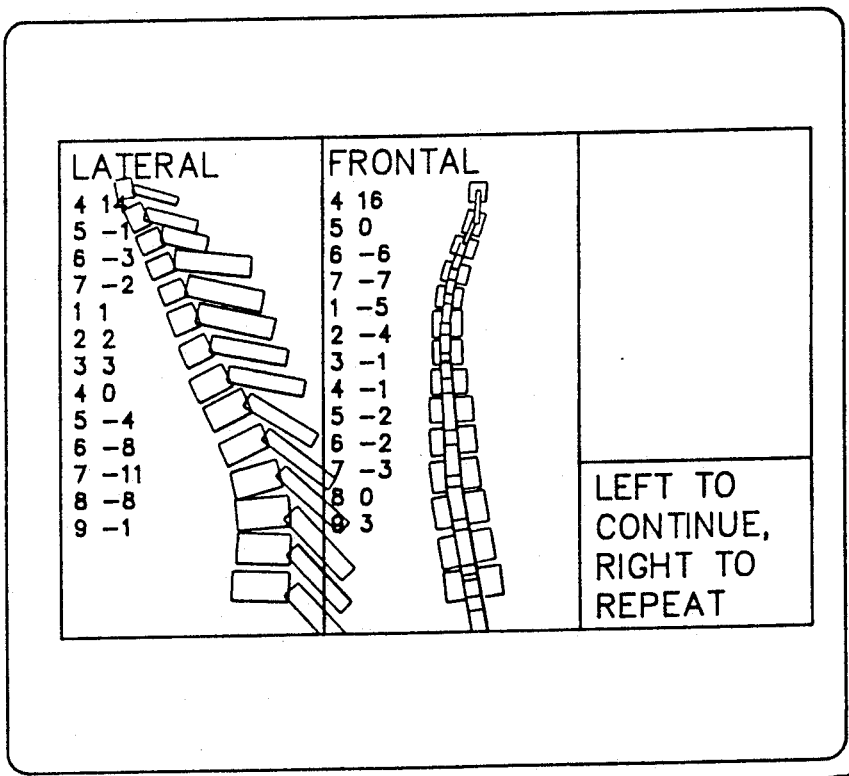

Once this procedure is complete, the frontal plane and orientation of the patient has been defined and the system will prompt the surgeon to define the vertebral levels between which the desired measurement is to occur. This is necessary since often limited exposure of the spine permits direct measurement of only a specific segment. Once the beginning and ending vertebrae are defined, this system will prompt the surgeon to proceed with a scan of the vertebra. This scan is performed by placing the digitizer tip along the line defining the centers of the vertebral bodies. The system will then present a graphics representation of a generic spine with the curvature calculated as per the digitized points shown in FIG. 18. The numeric listing represents the estimated angle of each vertebra.

Selection of item 4 of the Main Menu of Table 1 will result in the presentation of the Stereotaxic Menu. The primary application of the Stereotaxic Menu is the location and identification of unexposed parts such as hidden tumors, etc. and definition of their location with respect to a treatment instrument. The Stereotaxic Menu is illustrated in Table 5 below.

TABLE 5
STEREOTAXIC MENU

*1 - Object Location Menu
2 - Blind Hole Location
3 - Implant Orientation
4 - Return to Main Menu Selection of item 1 of the Stereotaxic Menu will result in the presentation of the Object Location Menu shown in Table 6 below.

TABLE 6
OBJECT LOCATION MENU

*1 - Read Object File
2 - Global Digitization
3 - Mount Probe Holder
4 - Mount Probe
5 - Locate Object
6 - Create Locator Data File
7 - Return to Main Menu This menu contains the five steps needed to locate a hidden object once identified in 3-dimensions by an imaging device such as a CAT scan. The imaging data is stored in a data file which is read by selecting item 1 of the Object Location Menu.

Selection of item 1 of the Object Location Menu will result in the reading of an object file from the patient diskette of the computer 23. The object file contains information typically obtained from CAT scans or MRI scans defining the location of an unexposed part with respect to three predetermined radiopaque markers which are still on the patient.

Selection of item 2 of the Object Location Menu will prompt the user to digitize the three radiopaque landmarks in order to define the system of orientation of the component with respect to the co-ordinate system of the apparatus. The information from the object file which was read above is now converted to the new orientation with respect to the co-ordinate system of the apparatus. The user is now requested to identify an entry point through which the access to the unexposed part is to be attempted.

Selection of item 3 of the Object Location Menu will result in the user being prompted to mount a probe holder at end 7a of the electrogoniometer 7, and selection of item 4 will prompt the user to mount a probe in the probe holder. As usual, the probe will be calibrated and tested for orientation and reproducibility by insertion into holes 37 of reference block 9.

Selection of item 5 of the Object Location Menu will result in an objective or target screen presentation on the screen of monitor 19 which is similar to the screen displayed for a drilling target as illustrated in FIG. 13 herein except that the square and circle targeting symbols are of different colours. The probe would then be manipulated to align the targeting symbols with the cross hair axis of the targeting screen, for example as shown in FIG. 14, and the probe can then be inserted along the desired axis to the depth as indicated by the depth bar illustrated at 97 in FIG. 13. Once the target is reached, the treatment may be completed.

By selecting item 6 of the Object Location Menu, a locator data file may be created.

Selecting item 2 of the Stereotaxic Menu in Table 5 will result in a protocol menu for the location of blind holes as per Table 7 below.

TABLE 7

| BLIND HOLE LOCATION |
| --- |
| *1 - Measure Hole |
| 2 - Post - Proced. Hole Measure |
| 3 - Install Drill |
| 4 - Install Drill Bit |
| 5 - Drill Hole |
| 6 - Return to Main Menu |

The location of a blind hole is performed in two steps: First, prior to the use of an orthopedic device, for example a femoral nail in which exists a cross hole at a distal end, the orientation and position of the hole is measured using a reference attachment in item 1 of the menu in Table 7. Once the surgical procedure is completed, the same reference attachment is used to redefine the hole using item 2 of the menu of Table 7. For convenience, the ability to drill this hole is then included in this menu in a manner similar to that found in the Drill Menu.

The Implant Orientation Menu, item 3 of the Stereotaxic Menu of Table 5 and shown as Table 8 below, lists the various steps required for the measurement of skeletal features prior to the replacement in, for example, total joint arthroplasty and subsequently in the actual placement of these implants. This menu is particularly generic, however, and was designed for demonstration purposes of the acetabulum of a total hip. It will of course be understood that each type of implant can have its own particular protocol which can be selected from a library of surgical procedures and implant types. For example, the special attributes of revision surgery can be taken into consideration by special routines to assist in the removal of remaining bone cement amongst others. The apparatus of the present application is unique with its ability to learn and grow with the field to which it is contributing.

TABLE 8

| IMPLANT ORIENTATION |
| --- |
| *1 - Body Reference |
| 2 - Post Procedure Body Reference |
| 3 - Implant Mounting |
| 4 - Implant Placement |
| 5 - Return to Main Menu |

In selecting item 1 of Table 8 body referencing is performed by the attachment of a reference jig using the DSIS attachment. The skeletal points are then digitized.

Once the surgical procedure has proceeded to the point prior to the implant placement, the reference jig is redigitized. This step is performed to accommodate changes in patient body position which have occurred during the procedure. To obviate this step, a reference system could have been attached directly to the bone as illustrated in FIG. 10 herein.

With the selection of item 3 of Table 8, the implant mounting takes place. Specialized implant holders are used to orient the implant. In this step, the mounting devices are oriented with respect to the electrogoniometer 7 of FIG. 1.

Figure 19:
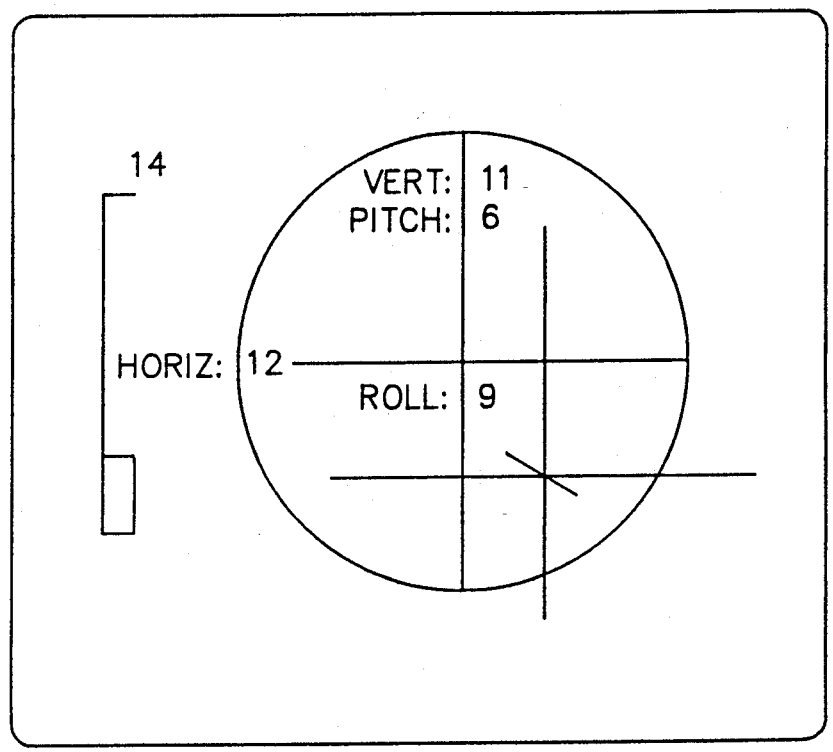
FIG. 19 is a screen display to aid in an implant placement procedure.

Selection Of item 4 of Table 8 precedes the implant placement step. In this step, the implant can be oriented using a display on the monitor 19 as illustrated in FIG. 19. Specific orientation with respect to the original digitized skeletal shapes can be obtained by observing the tilt and displacement numbers displayed.

It is once again emphasized that the Main Menu and sub-menus above-discussed are merely examples to illustrate the operation of the inventive apparatus. More items can be added to the Main Menu, or to the sub-menus of the Main Menu, for further surgical procedures as required. In addition, the menus can be amended to take into account changes in such surgical procedures. Accordingly, it can be seen that the apparatus of the present invention is flexible and has the ability to grow with additions and changes to surgical procedures.

Figure 20:
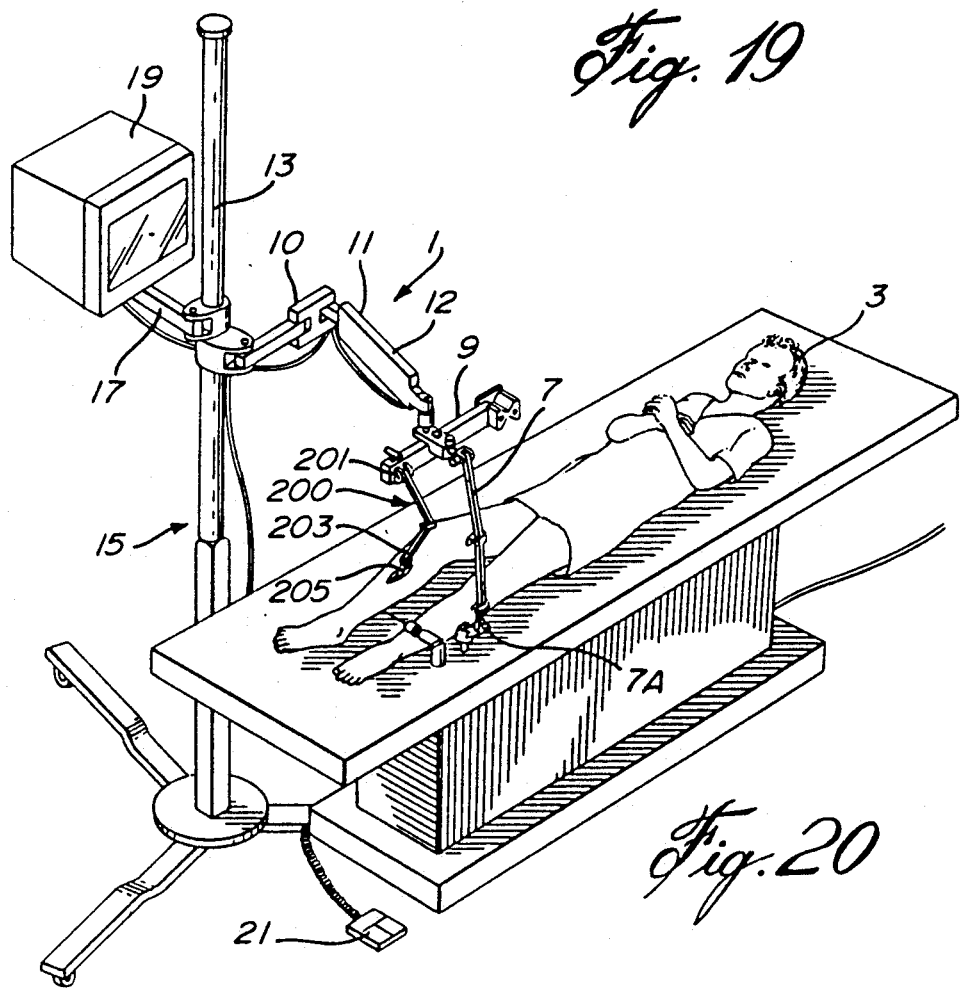
FIG. 20 illustrates an embodiment which is an alternative to the link illustrated in FIG. 10.

The link mechanism as illustrated in FIG. 10, because it is rigid, does not always permit movement of the leg to which it is attached as may be required by the surgeon. In order to overcome these restraints, an alternative embodiment for the link, to provide a known separation and relationship between a portion of the patient on which surgery is to be performed and the surgical instrument is illustrated in FIG. 20. Referring to FIG. 20, the link comprises a goniometer 200, which may be similar to the goniometer 7, having a first end 201 and a second end 203. The first end 201 is connected to the reference block 9, and the second end 203 is connected to a self-indexing mechanism 205, for example, the DSIS illustrated in FIGS. 5 to 12 herein. With such a connection, the separation or relationship between the portion of the patient on which surgery is to be carried out and the surgical instrument is measurable in from 1 to 6 or even more degrees of freedom through a wide range of movements of the patient's leg. With this instrument, the position and orientation of the portion of the leg is followed in the three-dimensional coordinate reference system. Accordingly, the separation and relationship between the portion of the patient on which the operating procedures are to be performed and the reference floc, and therefore the surgical instrument, remains known even through this wide range of movements of the portion of the patient, for example, in FIG. 20, the leg of the patient.

Although specific embodiments have been described, this was for the purpose of illustrating, but not limiting, the invention. Various modifications, which will come readily to the mind of one skilled in the art, are within the scope of the invention as defined in the appended claims.

I claim:

1. A computer-aided surgical device, having an associated three-dimensional co-ordinate reference system, for aiding a medical practitioner is positioning a surgical instrument or implant when performing surgery on, or examining, portions of a orientations in or on said patient defined either by physical measurement of the positions and orientations, in said co-ordinate reference system, of said portions using said device, or by communication to said device, from an external 2- or 3-dimensional imaging information source, of the positions and orientations, in said co-ordinate reference system, of said portions, said measurement of said commutation defining two- or three-dimensional patient data of the position and orientation of said portions in said co-ordinate system;

whereby, said patient data identifies the position and orientation of said portions to which surgical procedures, or examinations, are to be applied;

said device comprising;

a reference means having a referenced point in the reference co-ordinate system thereon;

said reference means and said reference point being disposed outside of and apart from said patient;

means for determining the position and orientation of said portion on said patient in said co-ordinate reference system relative to said reference point and for developing two- or three-dimensional patient display data proportional to said position and orientation of said portion;

instrument position determining means including sensing means for sensing the position and orientation of said instrument or implant in said co-ordinate reference system relative to said reference point and for developing two- or three-dimensional instrument data proportional to said position and orientation of said instrument;

a display means;

means for converting said patient display data to objective signals for presenting an objective display on said display means, means for converting said instrument data to instrument signals for presenting the position and orientation of said instrument or implant on said display means;

and further including means for providing a known physical relationship between said portion on said patient and said reference point;

whereby, the position and orientation of said portion and the position and orientation of said instrument or implant are both displayed on said display means;

even when said patient is moved;

whereby, to guide said medical practitioner in manipulating said instrument.

2. A device as defined in claim 1 wherein said instrument position determining means comprises:

electrogoniometer means having a mounting end and an instrument end;

a reference means;

said electrogoniometer means being mounted, at its mounting end, on said reference means at a reference point, of said co-ordinate reference system, thereof, such that said electrogoniometer means is movable about said reference point;

said surgical instruments being mountable at said instrument end of said electrogoniometer means.

3. A device as defined in claim 2 and including means for mounting a surgical instrument at said instrument end of said electrogoniometer means to maintain a rigid connection and fixed orientation between said electrogoniometer means and said instrument.

4. A device as defined in claim 2 and including a reference block mounted adjacent the mounting end of said electrogoniometer, said reference block including instrument characteristic determining means for determining the position, orientation and length of a surgical instrument.

5. A device as defined in claim 4 wherein said instrument characteristic determining means comprises:

reference holes having a predetermined length and an orientation which is fixed relative to said reference point, whereby said holes extend in a first direction;

reference surfaces having an orientation which is fixed relative to said reference point, said reference surfaces extending in said first direction; and a V-groove drill reference whose orientation is fixed relative to said reference point, said V-groove extending between said reference surfaces.

6. A device as defined in claim 2 and further including:

a mounting means;

swingable arms mounted on said mounting means and swingable about said mounting post;

said reference means being connected to said mounting means by said swingable arms;

whereby said reference means is movable relative to said mounting means.

7. A device as defined in claim 1 wherein said means for determining the position and orientation of said portion comprises a mechanical linkage and a means for fixing said mechanical linkage to said patient.

8. A device as defined in claim 7 wherein said means for fixing said mechanical linkage to said patient comprises a double self-indexing screw comprising:

an elongated cylinder;

a screw extending centrally from one end of said elongated cylinder and being rotatable relative to said elongated cylinder;

two alignment pins extending from said one end of said elongated cylinder, said screw and said alignment pins being disposed in alignment.

9. A device as defined in claim 8 wherein said double self-indexing screw is connected to said mechanical linkage by a linear, spherical double self-indexing screw clamp comprising a ball joint and a clamping member;

the free end of said double self-indexing screw being received by said ball joint;

a shaft of said mechanical linkage being received by said clamping member.

10. A device as defined in claim 7 wherein said mechanical linkage comprises a plurality of clamping members interconnected by shafts;

each clamping member comprising at least one lateral opening for receiving a shaft and clamping means for fixedly clamping a received shaft to said clamping member.

11. A device as defined in claim 7 wherein said means for fixing said mechanical linkage to said patient comprises a saw-tooth, self-indexing screw comprising:

an elongated cylinder;

a screw extending centrally from one end of said elongated cylinder and being rotatable relative to said elongated cylinder:

said one end of said elongated cylinder comprising a saw-tooth arrangement.

12. A device as defined in claim 11 wherein said mechanical linkage comprises a plurality of clamping members interconnected by shafts;

each clamping member comprising at least one lateral opening for receiving a shaft and clamping means for fixedly clamping a received shaft to said clamping member.

13. A device as defined in claim 12 wherein said self-indexing screw is connected to said mechanical linkage by a linear, spherical self-indexing screw clamp comprising a ball joint and a clamping member;

the free end of said self-indexing screw being received by said ball joint;

a shaft of said mechanical linkage being received by said clamping member.

14. A device as defined in claim 1 wherein said means for determining the position and orientation of said portion comprises a second electrogoniometer and a means for fixing one end of said second electrogoniometer to said patient.

15. A device as defined in claim 14 wherein said means for fixing one end of said second electrogoniometer to said patient comprises a double self-indexing screw comprising:
  an elongated cylinder;
  a screw extending centrally from one end of said elongated cylinder and being rotatable relative to said elongated cylinder;
  two alignment pins extending from said one end of said elongated cylinder, said screw and said alignment pins being disposed in alignment.

16. A device as defined in claim 14 wherein said means for fixing one end of said second electrogoniometer to said patient comprises a saw-tooth self-indexing screw comprising:
  an elongated cylinder;
  a screw extending centrally from one end of said elongated cylinder and being rotatable relative to said elongated cylinder;
  said one end of said cylinder comprising a saw-tooth arrangement.

* * * * *